United States Patent [19]

Torchilin et al.

[11] Patent Number: 5,534,241
[45] Date of Patent: Jul. 9, 1996

[54] AMPHIPATHIC POLYCHELATING COMPOUNDS AND METHODS OF USE

[76] Inventors: Vladimir P. Torchilin, 41, 8th St., #3208, Charlestown, Mass. 02129; Vladimir S. Trubetskoy, 9 Morton Ter., Milton, Mass. 02186; Gerald L. Wolf, 5 Hawthorn Rd., Winchester, Mass. 01890

[21] Appl. No.: 96,083

[22] Filed: Jul. 23, 1993

[51] Int. Cl.$^6$ .................................................. A61B 5/055
[52] U.S. Cl. ...................... 424/9.321; 436/173; 424/450; 514/6; 514/54; 514/57; 514/60; 514/836; 530/400
[58] Field of Search ............................ 424/9, 450, 9.321; 436/173; 128/653.4, 654; 514/6, 54, 57, 60, 836; 530/400

[56] References Cited

U.S. PATENT DOCUMENTS

| | | | |
|---|---|---|---|
| 4,483,929 | 5/1982 | Szoka | 436/533 |
| 4,920,016 | 12/1987 | Allen et al. | 424/450 |
| 4,927,637 | 5/1990 | Morano et al. | 424/450 |
| 5,000,960 | 3/1991 | Wallach | 424/450 |
| 5,135,737 | 8/1992 | Keana | 424/9 |
| 5,223,242 | 6/1993 | Khaw et al. | 424/1.1 |
| 5,230,883 | 7/1993 | Komguth et al. | 424/9 |
| 5,312,617 | 5/1994 | Unger et al. | 424/9 |
| 5,364,614 | 11/1994 | Platzek et al. | 424/9 |
| 5,368,840 | 11/1994 | Unger | 424/9 |
| 5,370,860 | 12/1994 | Elgavish et al. | 424/4 |

OTHER PUBLICATIONS

Grant et al., "A Liposomal MRI Contrast Agent: Phosphatidylethanolamine–DTPA," *Magnetic Resonance in Medicine*, 236–243 (1989).

Klibanov et al., "Amphipathic polyethyhleneglycols effectively prolong the circulation time of liposomes," FEBS 08706, 268:35–37 (1990).

Tilcock et al., "Liposomal Gd–DTPA: Preparation and Characterization of Relaxivity," *Radiology* 171:77–80 (1989).

Torchilin et al., "Antibody–Linked Chelating Polymers for Immunoimaging In Vivo," *Journal of Controlled Release*, 11:297—303 (1989).

Torchilin et al., "Targeted accumulation of polyethylene glycol–coated immunoliposomes in infarcted rabbit myocardium," *Research Communications* 6:2716–19 (1992).

Primary Examiner—Gary E. Hollinden
Attorney, Agent, or Firm—Fish & Richardson

[57] ABSTRACT

An amphipathic polychelating compound including a hydrophilic polymeric moiety having a main backbone and a plurality of reactive side groups, a lipid-soluble anchor linked to the N terminal of the polymeric moiety, and a plurality of chelating agents linked to the side groups of the polymeric moiety. The polychelating compounds are bound to liposomes or micelles for use as diagnostic and therapeutic agents.

16 Claims, 5 Drawing Sheets

AMPHIPATHIC POLYCHELATING COMPOUNDS AND METHODS OF USE

BACKGROUND OF THE INVENTION

This invention relates to amphipathic polychelating compounds for use in liposomes or micelles.

Liposomal contrast agents for magnetic resonance imaging (MRI) or radioscintigraphic imaging of organs in the so-called macrophage-monocyte system, such as the liver, spleen, lymph nodes, and bone marrow, can be prepared by encapsulating water-soluble metal-chelator complexes into the aqueous interior of liposomes as described in Tilcock, et al., *Radiology*, 171:77–80 (1989). However, once introduced into the body of a patient, the interaction of the liposomes with body fluids may induce the leakage of the chelator complexes out of the liposomes and cause artifacts in diagnostic images. In addition, the high concentrations of labeled chelator complexes inside the liposomes that are required for an adequate enhancement of the image also decrease the amount of water within the liposomes, which tends to decrease the relaxivity of the label, and hence the signal intensity.

Contrast agents can also be prepared with amphipathic chelating agents that are physically incorporated into the lipid bilayer membranes of liposomes. See, e.g., Grant et al., *Magn. Res. Med.*, 11:236–243 (1989); Kabalka et al., *Magn. Res. Med.*, 8:89–95 (1988); and Hnatowich et al., *J. Nucl. Med.*, 22:810–816 (1981). However, such known amphipathic chelating agents bear only one metal or paramagnetic ion per lipid molecule. When such chelating agents include paramagnetic labels such as gadolinium (Gd) for use in MRI, they require highly concentrated lipid suspensions to form liposomes with an increased molar content of the chelating agent in order to provide a useful image. However, this can result in liposomes having unstable lipid bilayers.

SUMMARY OF THE INVENTION

The invention relates to novel amphipathic polychelating compounds which can bind a plurality of ions, and features an amphipathic polychelating compound, e.g., in lyophilized form, that includes a hydrophilic polymeric moiety having a main backbone and a plurality of reactive side groups, a lipid-soluble anchor linked to the N terminal of the polymeric moiety, and a plurality, e.g., 2 to 200, and preferably 5 to 50, of chelating agents linked to the side groups of the polymeric moiety.

As used herein, the term "linked" means covalently or non-covalently bonded, e.g., by hydrogen, ionic, or Vander-Waals bonds. Such bonds may be formed between at least two of the same or different atoms or ions as a result of redistribution of electron densities of those atoms or ions. The term linked also covers the "coordination bonds" that bind an ion into a chelating agent, the interaction of a lipid-soluble anchor with the lipids in a micelle to secure a polychelating compound to the micelle, and hydrophobic bonds.

The backbone of the polymeric moiety can be a polyamino acid, e.g, poly-L-lysine, protein, activated polysaccharide, reactive synthetic polymer, or reactive derivative thereof.

The lipid-soluble anchor can be a phospholipid, e.g., phosphatidyl ethanolamine, phosphatidyl inositol, glycolipid, long-chain fatty acid, cholesterol, a long-chain, polar, lipid-soluble molecule having more than 5 carbon atoms in the chain, stearylamine, or reactive derivative thereof.

A "derivative" means a compound or molecule whose core structure is the same as, or closely resembles that of, a parent compound, but which has a chemical or physical modification, such as a different or additional side groups, which allows the derivative to be linked to another molecule. The term includes copolymers of parent compounds that can be linked to other atoms or molecules.

In a preferred polychelating compound, the polymeric moiety is poly-L-lysine, the lipid-soluble anchor is N-glutaryl-phosphatidyl-ethanolamine, and the chelating agent is diethylene triamine-pentaacetic acid.

In another embodiment, the invention features a micelle including lipids and a polychelating compound linked to the lipids via the lipid-soluble anchor, or a micelle formed of the polychelating compound itself.

The invention also features a liposome including a lipid bilayer membrane and a polychelating compound bound to the membrane via the lipid-soluble anchor. This liposome can further include a plurality of ions bound to the chelating agents, and may be modified with a targeting group, e.g., an antibody, bound to the membrane. The liposomes can also be modified with a protective polymer bound to the membrane. Such protective polymers are water-soluble, have a chain length longer than that of the hydrophilic polymeric moiety, and have a molecular weight of from, e.g., 500 to 40,000 daltons. Representative polymers include derivatives of polyethylene glycol (PEG), polypropylene glycol (PPG), polyacrylamide, poly N-vinyl pyrrolidone, polyacrylic acid, polyalcohol, ganglioside, polyamino acid, polysaccharide, polyamidoamine, polyethyleneamine, or a copolymer or block copolymer thereof.

As used herein, a compound or group is "bound" to a liposome membrane when it is chemically or physically attached to the membrane, e.g., by the intercalation of a lipid-soluble anchor into the membrane itself, or by binding directly to active groups of membrane lipids, thus using a preexisting "anchor."

Lipid membrane components are any lipid-soluble molecules that can form a lipid bilayer membrane or a micelle including, e.g., phospholipids, glycolipids, cholesterol, and derivatives thereof.

In another embodiment, the invention features a reagent kit including lipids and an amphipathic polychelating compound of the invention. Such kits may also include targeting groups and/or protective polymers including lipid-soluble anchors. All of the components in the kit can be in lyophilized form.

In yet a further embodiment, the invention features a method of imaging a target region in the body of a patient by administering a diagnostically effective amount of liposomes to the patient, the liposomes including lipid bilayer membranes, the polychelating compounds of the invention bound to the membranes, and a plurality of labeling ions linked to the chelating agents on the polychelating compounds, allowing sufficient time for the liposomes to accumulate in the target region, and obtaining an image of the target region by detecting the labeling ions in the region. The liposomes can be modified with protective polymers, and/or targeting groups.

A "diagnostically effective amount" of the polychelating compound, or a suspension of liposomes containing the compound, is an amount that will provide an image of a target region in the patient.

As used herein, "image" means a visual picture of a region within a patient that results from MRI, radioscintigraphy, and X-ray imaging.

The invention also features a method of radiotherapy for treating a target region in the body of a patient by administering a therapeutically effective amount of liposomes to the patient, the liposomes including lipid bilayer membranes, the polychelating compounds of the invention bound to the membranes, and a plurality of radioactive ions linked to the chelating agents on the polychelating compounds, and allowing the liposomes to accumulate in the target region to effect radiotherapy of the region.

The invention further features a method of chelating a target region in the body of a patient by administering a therapeutically effective amount of liposomes to the patient, the liposomes including lipid bilayer membranes, and polychelating compounds of the invention bound to the membranes, the polychelating compounds having no ions linked to the chelating agents upon administration, and allowing the liposomes to accumulate in the target region to effect chelation of metals in the region.

A "therapeutically effective dose" of the polychelating compound, or of liposomes containing the compound, is an amount that will provide a therapeutic benefit to a target region in the patient.

Other features and advantages of the invention will be apparent from the following detailed description in conjunction with the claims and the drawings.

DETAILED DESCRIPTION

The drawings are first briefly described.

Amphipathic Polychelating Compounds

Amphipathic polychelating compounds include three components: (1) a hydrophilic polymeric moiety, (2) a lipid-soluble anchor linked to the amino (N) terminal of the polymeric moiety, and (3) a chelating agent linked to side groups on the polymeric moiety.

Polymeric Moieties

The hydrophilic polymeric moiety can be any pharmacologically acceptable, water-soluble, natural or synthetic polymer that includes a polymeric backbone with multiple reactive side groups that can be activated and covalently linked to a chelating agent. For example, any activated polysaccharides, polyamino acids, or synthetic polymers that include free carboxyl or amino groups for linking to a chelating agent are suitable. The following list summarizes polymeric backbones suitable for use in the present invention:

Proteinaceous backbones
    Individual proteins
        albumins
        globulins
        soluble extracellular matrix proteins (e.g. fibronectin)
        fibrinogen
        thrombin
    Plasma protein mixtures
        plasma
        plasma fractions
    Glycoproteins
    Chemically modified proteins
    Recombinant proteins or peptides
Sugar containing backbones
    Carboxylated polysaccharides
        polymannuronic acid
        polygalacturonic acid
        polyguluronic acid
    Aminated polysaccharides
        glycosaminoglycans
    Activated polysaccharides
        dextran derivatives
        starch derivatives
Synthetic backbones
    Polylysines
    Polyethyleneimines
    Polyethylene glycol and its derivatives
    Polypropylene glycol and its derivatives
    Polyacrylic acids
    Soluble polyelectrolytes
    Soluble polymers/copolymers of the vinyl series The term "chemically modified protein" means a protein molecule in which at least one chemical bond is produced or eliminated within the molecule. The term includes proteins which are, e.g., acylated, glycosylated, deglycosylated, oxidized, reduced, fractionated into peptide fragments, or phosphorylated.

The most preferred backbones for the polymeric moiety are polyamino acids, e.g., poly-l-lysine, poly-d-lysine, poly-α,β-(2-aminoethyl)-D,L-aspartamide, or poly-l-aspartic acid, because of their known tissue compatibility, large number of reactive groups, and relatively low cost. Polyamino acids may be natural or synthetic, are preferably non-proteinaceous, and are prepared by chemical synthesis or by recombinant techniques, such as genetic engineering.

Lipid-Soluble Anchors

The lipid-soluble anchor can be any water-insoluble, polar, lipid-soluble molecule that is easily miscible with components of natural or synthetic lipid bilayer membranes or lipid micelle monolayers, e.g., phospholipids, phosphoglycerides, and glycolipids. For example, the lipid-soluble anchor may be a phospholipid, e.g., phosphatidyl ethanolamine (PE), or phosphatidyl inositol (PI), a glycolipid, e.g., a ganglioside, cholesterol and its derivatives, e.g., cholesteryl chlorocarbonate, or a long-chain saturated or unsaturated fatty acid or other long-chain, polar, lipid-soluble molecule, having at least 5, and preferably at least 10, carbon atoms, e.g., palmitic, stearic, myristic, or oleic acids, and derivatives thereof.

Chelating Agents

The chelating agent can be any molecule that includes a structure which can form so-called "coordination bonds" to bind a metal or paramagnetic ion. These chelating agents must typically be modified or derivatized to link to the reactive side groups of the polymeric moiety. Suitable chelating agents for binding to the polymeric moiety include diethylene triamine-pentaacetic acid (DTPA), 1,4,7,10-tetraazacyclododecane-N,N,N',N'''-tetraacetic acid (DOTA), ethylene-diaminetetraacetic acid (EDTA), 1,4,7,10-tetraazacyclotetradecance-N,N',N''-triacetic acid (DO3A), 1,4,7-triazacyclononane-N,N',N''-triacetic acid (NOTA), 1,4,8,11-tetraazacycloteradecane-N,N',N',N'',N'''-tetraacetic acid (TETA), hydroxybenzylethylene-diamine diacetic acid (HBED), and deferoxamine. This list is exemplary, and any variety of chelating agents could be used, depending on the desired labeling ion.

These chelating agents can bing various labeling ions for different applications as exemplified below:

Paramagnetic label (for MR imaging)
  Gadolinium
  Manganese
  Iron
  Dysprosium
  Holmium
  Copper
  Europium
  Erbium
  Chromium
  Nichel
  Cobalt Superparamagnetic labels (for MR imaging)
  Magnetites
  Superparamagnetic iron oxides
  Monocrystalline iron oxides Radioactive labels (for imaging or therapy)
  $^{111}$Indium
  $^{99m}$Technetium
  $^{67}$Gallium
  $^{51}$Chromium
  $^{57}$Cobalt
  $^{99}$Molybdenum
  $^{64}$ or $^{67}$Copper
  $^{201}$Thallium
  $^{90}$Yttrium
  $^{186}$ or $^{188}$Rhenium
  $^{153}$Samarium
  $^{165}$Dysprosium
  $^{212}$Bismuth
  $^{211}$Astatine Radiopaque labels (for X-ray imaging)
  Radiopaque metals and their salts (e.g. Ag, Au)

The amount of label to be added to the polychelating compounds depends on the nature of the label, and the use of the compounds. For example, when the polychelating compounds are used to treat metal, e.g., lead, poisoning, they are administered without any labeling ions, but chelate metals in the patient. For gadolinium containing compounds, a concentration of about 40 mmol of Gd per estimated volume of the target, e.g., an organ, or part thereof to be imaged, has been found to provide a clear MR image. This concentration is achieved by a dosage of about 0.1 to 0.2 mmol Gd/kg of body weight of the patient. For radioactive compounds, an injection of liposomes having a radioactivity of e.g., 100 to 300 µCi in rabbits, 0.5 to 2 mCi in dogs, and 3 to 5 mCi in humans has been found to provide a clear gamma-ray image.

Synthesis of the Polychelating Compounds

Figure 1:
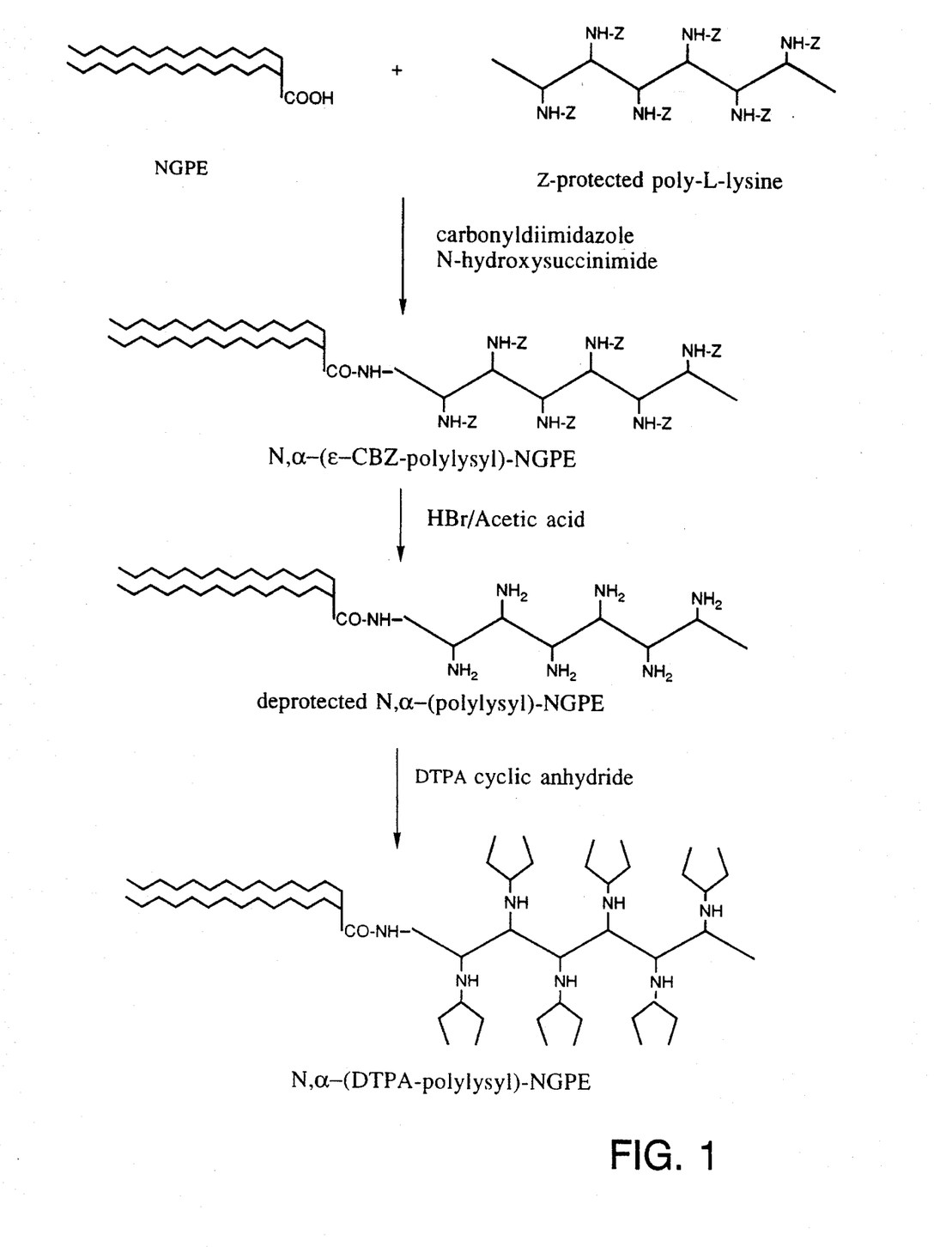
FIG. 1 is a flowchart of the synthesis of an amphipathic polychelating compound.

As shown in the flowchart of FIG. 1, the polychelating compound N,α,-(DTPA-polylysyl)-NGPE was synthesized by modifying the single N terminal amino group of the hydrophilic polymeric moiety, benzyloxycarbonyl-protected polylysine, with a lipid-soluble anchor, NGPE, followed by deprotection with HBr/acetic acid and modification with a chelating agent, DTPA anhydride.

In particular, NGPE (25 mg, Avanti Polar Lipids, Birmingham, Al) was activated with N,N'-carbonyldiimidazole (25 mg, Aldrich) in the presence of N-hydroxysuccinimide (11.4 mg, Pierce) for 16 hours at room temperature. Other activation schemes are known. Thereafter, ε,N-carbobenzoxy poly-L-lysine (100 mg, Sigma, MW 3,000 Da) and triethylamine (10 ml, Pierce) were added to the initial mixture, and the reaction was allowed to proceed for another 5 hours at room temperature with stirring. Thin layer chromatography demonstrated full conversion of initial NGPE ($R_f$=0.37 in $CHCl_3$:$CH_3OH$:$H_2O$=65:25:4) into the product, N,60-(ε-CBZ-polylysyl)-NGPE, ($R_f$=0.59 in the same system) as detected with phosphate staining. The product was precipitated with water, washed, and freeze-dried (lyophilized).

The lyophilized N,α-(ε-CBZ-polylysyl)-NGPE (67.4 mg) was dissolved in 3 ml of a 30% hydrogen bromide solution in glacial acetic acid (Aldrich) to remove the protective groups. The reaction was allowed to proceed for 2 hours at room temperature. Deprotection results in an amphipathic molecule with a lipid-soluble anchor and a bulky hydrophilic polymeric moiety. Deprotected N,α-polylysyl-NGPE was precipitated with dry ethyl ether, washed with the same solvent and freeze-dried.

After this deprotection step all side amino groups of the polylysine moiety can be linked to a modified chelating agent, e.g., DTPA anhydride, allowing a plurality of DTPA groups to be bound to each polychelating compound. For example, when the degree of polymerization of the polymeric moiety, e.g., polylysine, is 11, it is possible to introduce up to 11 DTPA groups per polychelating compound. Higher degrees of polymerization will allow binding of greater numbers of chelating agents, e.g., from 2 to 200, and preferably from 5 to 50, for each polychelating compound. This labeling ratio is superior to the one metal atom per compound ratio for previously known contrast agents.

In particular, the lyophilized N,α-polylysyl-NGPE (37 mg) was suspended in a chloroform:methanol (1:1) mixture and reacted with DTPA anhydride (100 mg in 2 ml of methylsulfoxide, Aldrich) in the presence of 5 ml of triethylamine for 16 hours at room temperature with stirring to produce the desired amphipathic polychelating compound, N,α-(DTPA-polylysyl)-NGPE. Thereafter, succinic anhydride (100 mg in 0.2 ml methylsulfoxide) was added to block any remaining free amino groups on the polylysine. The N, N--(DTPA-polylysyl)-NGPE was purified from any water-soluble compounds by dialysis against deionized water and then freeze-dried to give a yield of 31.5 mg.

To label the polychelating compound, 25 mg of the lyophilized product was suspended in 2 ml of dry pyridine and labeled with the gadolinium containing $GdCl_3$-$6H_2O$ (150 mg in 0.25 ml of 0.1 citrate, pH 5.3, Aldrich). After 2 hours of incubation at room temperature with stirring, the reaction mixture was dialyzed against deionized water and freeze-dried to yield 48 mg of labeled Gd-(DTPA-polylysyl)-NGPE.

Preparation of Liposomes

Figure 2:
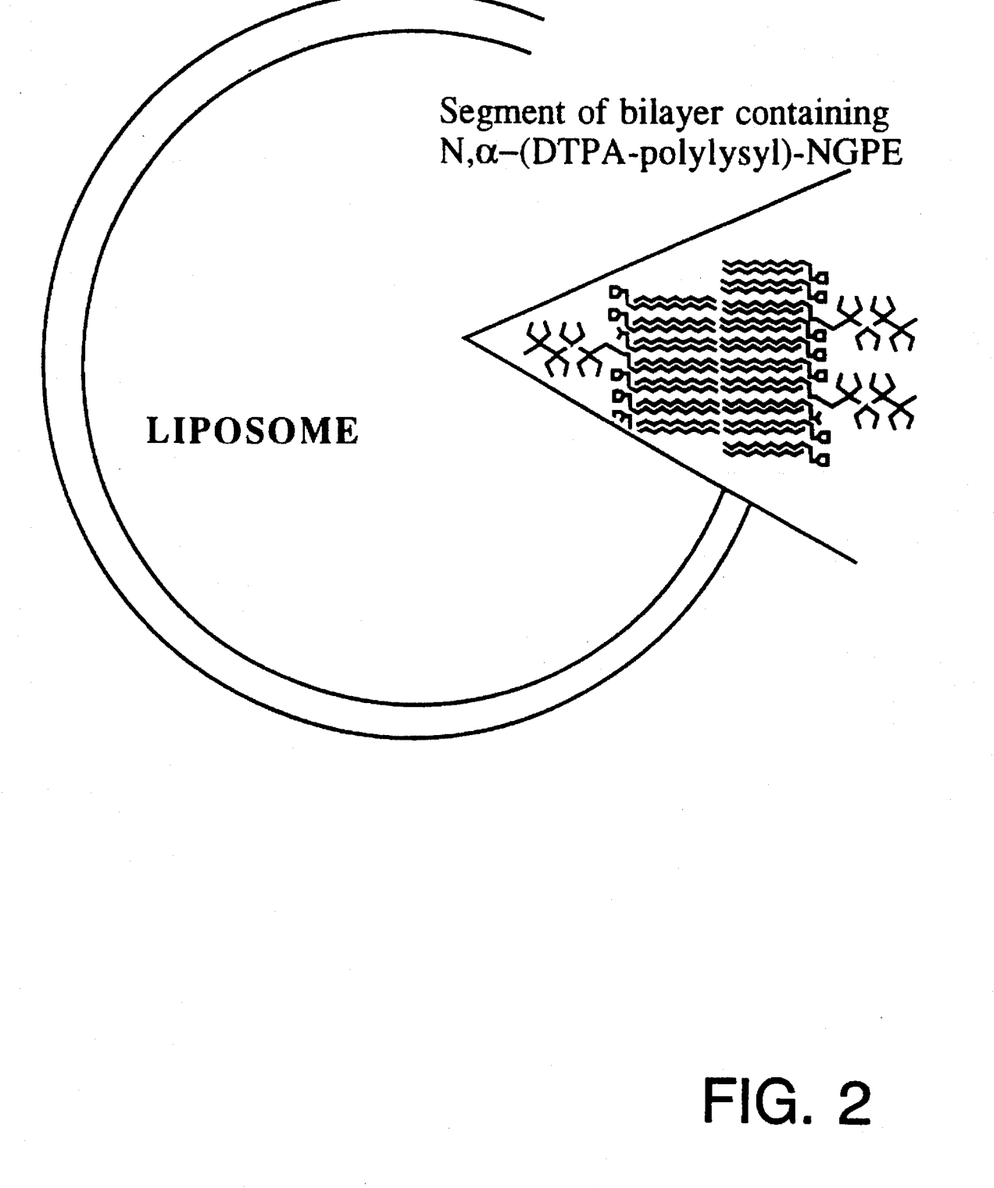
FIG. 2 is a schematic showing the incorporation of the polychelating agent N,α,-(DPTA-polylysyl)-NGPE into a liposome.

FIG. 2 schematically shows the binding or incorporation of N,α-(DTPA-polylysyl)-NGPE into a liposomal bilayer membrane, which can then be labeled with, e.g., gadolinium. Of course, previously labeled Gd-(DTPA-polylysyl)-NGPE can also be incorporated into liposomes, but it is preferred to form the liposomes containing the polychelating compound, and then to label the liposomes just prior to injection into a patient. In addition, the polychelating compounds can be formed into, or linked with, lipid micelles.

Upon incorporation into the lipid bilayer of a liposome, or the lipid monolayer of micelles, the polymeric moiety of the polychelating compound forms a "coat" of numerous chelated metal or paramagnetic ions on the surface of the liposome or micelle, which are available for contact with exterior water environment.

In particular, liposomes containing Gd-(DTPA)-polylysyl-NGPE were prepared by a freeze-drying method in which an organic solution of membrane components, i.e., egg lecithin (phosphatidyl choline, Avanti Polar Lipids) and cholesterol (Sigma) in a 75:25 molar ratio, was dried under an argon stream and further desiccated under vacuum to produce a lipid film. A suspension of lyophilized Gd-(DTPA)polylysyl-NGPE in deionized water was added to the lipid film and vortexed. The lipid/water mixture was sonicated in bath-type sonicator (Laboratory Supplies, Inc.) for 5 min. to form intermediate liposomes, and freeze-dried overnight.

The lyophilized lipid-polychelating compound mixture was reconstituted with HEPES buffered saline, pH 7.4, vortexed, and extruded consecutively through polycarbonate filters with 0.6, 0.4 and 0.2 μm pore size (Poronics) to form liposomes with an average diameter of 0.2 μm, e.g., as described in U.S. Pat. No. 4,927,637, which is incorporated herein by reference. These final liposomes can be lyophilized for long-term storage in powder form, e.g., for use in a kit that includes materials necessary for the diagnostic or therapeutic use of the liposomes as discussed below.

This freeze-drying method for liposome preparation is preferred because of the insolubility of the Gd-(DTPA) polylysyl-NGPE in water or organic solvents. However, other liposome preparation methods that result in the incorporation of hardly soluble amphiphilic substances into the bilayer are known and can also be used.

For comparison studies, DTPA-stearylamine (DTPA-SA) and DTPA-phosphatidylethanolamine (DTPA-PE) were synthesized as described in Hnatowich et al., *J. Nucl. Med.*, 22:810–814 (1981) and Grant et al., *Magn. Res. Med.*, 11:236–243 (1989), respectively, which are both incorporated herein by reference, and loaded with Gd as described above for Gd-(DTPA-polylysyl)-NGPE. Liposomes containing Gd-DTPA-SA or Gd-DTPA-PE were prepared using the freeze-drying method described above.

In Vitro Studies

The performance of the amphipathic polychelating compounds as MRI contrast agents was compared with that of previously known contrast agents by preparing liposomes (egg lecithin:cholesterol=1:1) containing 3 mol % of either one of two known amphipathic Gd-labeled contrast agents, Gd-DTPA-PE and Gd-DTPA-SA, or Gd-(DTPA-polylysyl)-NGPE. The NMR relaxation parameters of all three liposome preparations were measured in vitro in a RADX NMR Proton Spin Analyzer at 5 MHz. Gadolinium determinations were performed by Galbraith Laboratories, Inc. (Knoxville, Tenn.) using an atomic absorption flame photometer.

Figure 3:
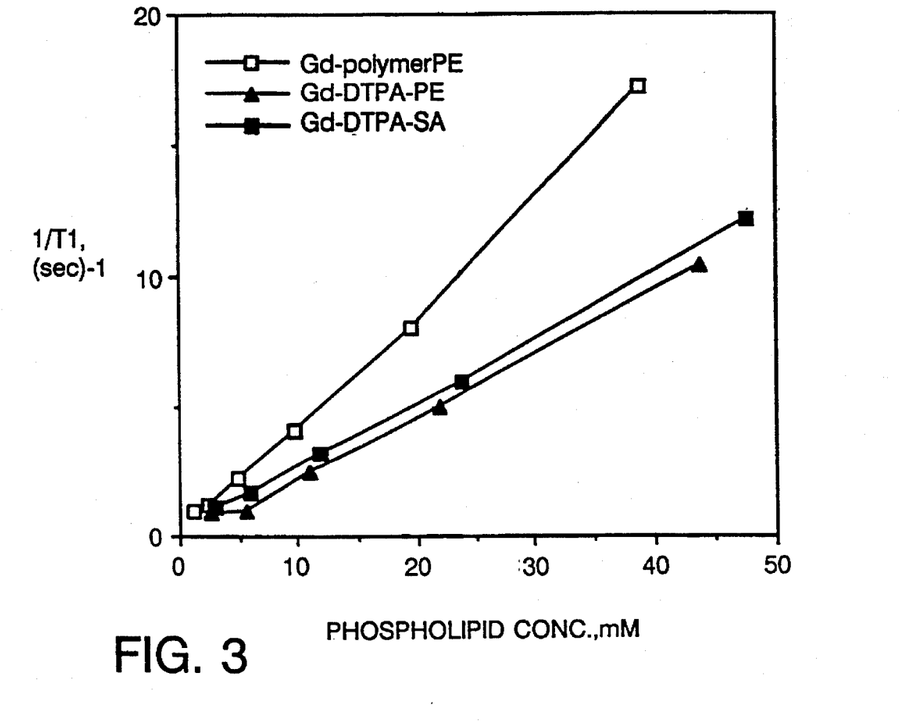
FIG. 3 is a graph showing the molecular relaxivities ($T_1$) of Gd-(DPTA-polylysyl)-NGPE, Gd-DTPA-phosphatidyl-ethanolamine (PE), and Gd-DTPA-stearylamine (SA).

As shown in FIG. 3, the polychelating compound (□) has a paramagnetic relaxation influence on water protons which is twice as high as that of either Gd-DTPA-PE (▲) or Gd-DTPA-SA (■). Furthermore, the Gd content of the three liposome preparations used in this study was determined to be 18.25% for Gd-DTPA-PE, 17.72% for Gd-DTPA-SA, and 40.32% for the polychelating compound of the invention. This 40.32% (w/w) of Gd corresponds to 8–10 metal atoms per lipid-modified polymeric moiety assuming its molecular weight to be 3,500 to 4,000 Da.

Figure 4:
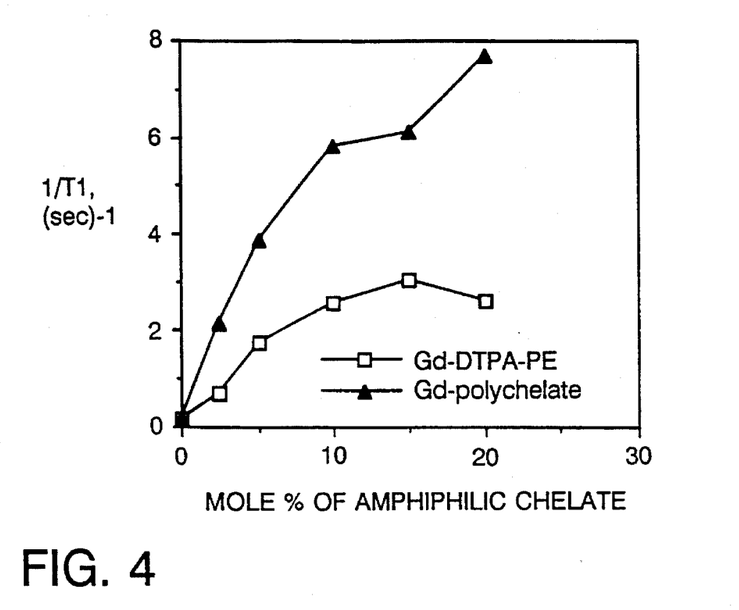
FIG. 4 is a graph showing the dependence of reverse $T_1$ on the amount of chelating agent in a liposomal membrane for Gd-(DPTA-polylysyl)-NGPE and Gd-DTPA-PE.

The inverse $T_1$ (the spin-lattice or longitudinal relaxation time) response of the amphipathic polychelating compound and that of Gd-DTPA-PE were studied to determine the dependence of the membrane density of these compounds on the relaxivity of the liposomes. As shown in FIG. 4, Gd-DTPA-PE (□) was found to have an optimum at approximately 15 molar % for egg PC/cholesterol liposomes. This finding is consistent with results of Grant et al., supra, who found that liposomes with 12.5 molar % of Gd-DTPA-PE result in maximal preparation relaxivity, and explained the phenomenon observed by closeness of Gd atoms to one another at elevated Gd-DTPA-PE concentrations.

It is interesting to note that Gd-(DTPA-polylysyl)-NGPE liposomes (▲) of the invention did not possess a relaxivity maximum in the concentration range under study, which indicates a possible increase compared to Gd-DTPA-PE or Gd-DTPA-SA in inter-metal atom distances on the liposome membrane.

Animal Studies

Figure 5A:
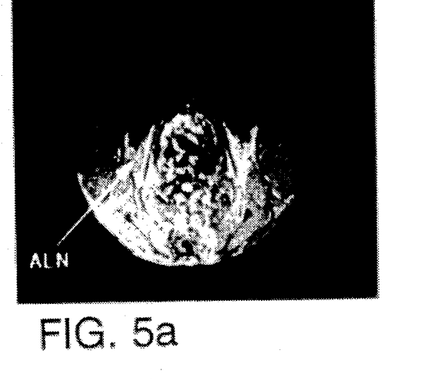
FIG. 5A is a transverse MRI scan of the axillary/subscapular lymph node area of a rabbit before injection of a contrast agent.
Figure 5B:
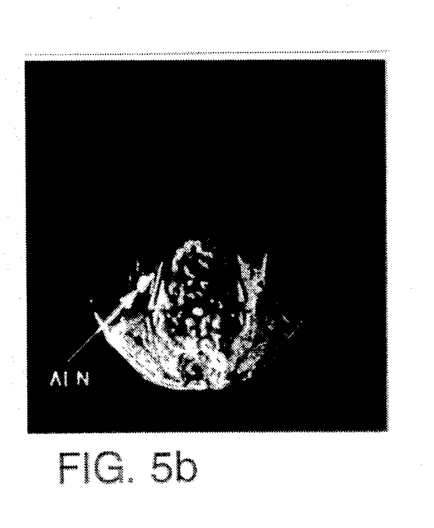
FIG. 5B is the same view as FIG. 5A, but taken 5 minutes after injection of liposomes containing 5 mol % of Gd-(DPTA-polylysyl)-NGDE.

To prove the efficiency of Gd-(DTPA-polylysyl)-NGPE liposomes as MRI contrast agents, lymph node visualization was performed on NZW rabbits using 100 mg of egg PC/cholesterol (75:25) liposome suspension containing 5 molar % of Gd-poly-NGPE. Animals were sedated with an intramuscular injection of Ketamine (40 mg/kg) and Xylazine (5 mg/kg). A suspension of the liposomes (0.5 ml, 20 mg of total lipids (3–5 mg of Gd) in HEPES buffered saline) was administered subcutaneously into the right forepaw. MRI images were taken after injection using a GE Signal MRI instrument at 1.5 Tesla ($T_1$ weighted pulse sequence, fat suppression mode). A rabbit transverse scan (FIG. 5B) demonstrates that the axillary and subscapular lymph node (ALN) can be seen on the scan taken just 5 minutes after injection demonstrating suitability of this preparation for MRI lymphography, where nothing is seen prior to injection (FIG. 5A).

The systemic behavior of the liposomes after intravenous injection into a rabbit was assessed by $^{111}$In labeling and subsequent radioscintigraphic detection using an Ohio Nuclear Sigma 410 gamma camera. DTPA-SA was added in trace amounts to the lipids used for the Gd-(DTPA-polylysyl)-NGPE liposome preparation mixture, and labeled with $^{111}$In by a known transchelation method described in Torchilin et al., *FASEB J.*, 6:2716–19 (1992). The $^{111}$In-liposomes (100–300 μCi) were administered intravenously into an anesthetized rabbit and images were taken for 2 hours after injection.

Figure 6:
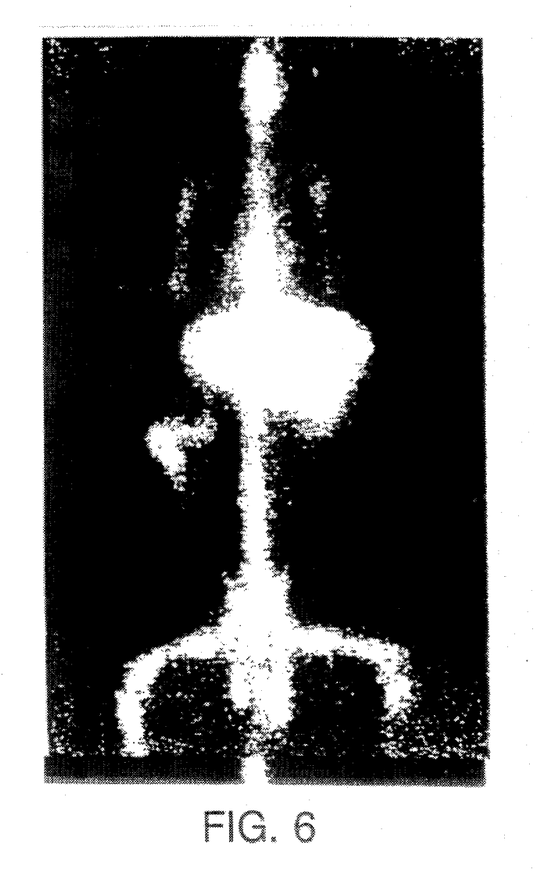
FIG. 6 is a whole body gamma-scintigram of a rabbit 2 hours after intravenous injection of $^{111}$in-labeled Gd-(DPTA-polylysyl)-NGPE.

FIG. 6 shows a whole body radioscintigraphy scan taken 2 hours after intravenous injection. The label accumulation sites were those expected for conventional liposomes: liver, spleen, lymph nodes, and bone marrow. However, other organs can be imaged using antibody-mediated targeting of

Modified Liposomes Containing Amphipatic Polychelating Compounds

The liposomes or micelles containing the amphipathic polychelating compounds can be further modified to alter the natural targeting of liposomes for the macrophage-monocyte system, e.g., liver, spleen, bone marrow, and lymph nodes. For example, liposomes can be modified with a surface-bound targeting group, such as an antibody, to target a particular organ or tissue within the body. Moreover, the liposomes can be modified to include protective polymers to reduce the normal uptake of the liposomes by the macrophage-monocyte system, to significantly increase the circulation time, or half-life, within the body.

Targeting Groups Bound to Liposomes

To obtain a liposome or micelle that is targeted for a specific antigen tissue, organ, or in the body, a targeting group is bound to the lipid membrane surface of the liposome, or linked to the micelle. For example, the carbohydrate portion of the membrane is oxidized, e.g., by exposure to sodium metaperiodate to yield aldehyde groups, which are highly reactive and will bind the target group to the membrane. In addition, the target group can be linked to a lipid-soluble anchor as described above, and the anchor is then intercalated into the liposome membrane. These and other methods of binding targeting groups to liposome membranes are described in U.S. Pat. No. 4,483,929, which is incorporated herein by reference. These methods are suitable for use with liposomes containing the amphipathic polychelating compounds of the invention.

The targeting group can be a polyclonal or monoclonal antibody, a fragment of an antibody, a chimeric antibody, an enzyme, a quasi substrate of an enzyme, a lectin, or a saccharide ligand of a lectin, which are selected or designed to target a specific site in the body. For example, the monoclonal antibody R11D10 against human cardiac myosin heavy chains can be used to target liposomes for necrotic myocardium tissue, e.g., after cardiac infarction. Similarly, monoclonal antibody 9B9 against angiotensin-converting enzyme from human lung can be used to target liposomes for the lungs. Torchilin et al., *FASEB J.*, 6:2716–19 (1992); Torchilin et al., *J. Controlled Release*, 11:297–303 (1989).

The targeting group, which is typically a protein or polypeptide, is preferably bound to the liposome membrane via a lipid-soluble anchor as follows. The polychelating compound is mixed with lipid membrane components in an organic solvent and the mixture is desiccated to form a mixed lipid-polychelating compound film. This film is mixed with an aqueous suspension of the targeting group (modified to include a lipid-soluble anchor) to form liposomes containing both the polychelating compound and the targeting group bound to the membrane. The targeting group is added in this second step, because these groups are often insoluble in or inactivated by organic solvents. These liposomes can then be lyophilized to form a powder or stored in suspension.

Surface Modified Liposomes

Liposomes, with or without added targeting groups, can also be modified to include large water-binding "protective polymers" that are bound to the lipid bilayer membrane to form a protective surface layer which significantly decreases the uptake of the liposomes by the macrophage-monocyte system, e.g., as described in U.S. Pat. No. 4,920,016, which is incorporated herein by reference. Micelles may be similarly modified.

By reducing the rate of uptake, the liposomes remain in the circulation much longer than unmodified liposomes. This allows surface-modified liposomes containing the amphipathic polychelating compounds of the invention to be used as blood pool imaging agents, or as tumor-targeting agents, since it has been shown that liposomes with a prolonged circulation time accumulate efficiently in a solid tumor model system. Gabizon, et al., *P.N.A.S., USA*, 18:6949–53 (1988). In addition, the reduced uptake lowers the toxicity of the liposomes by preventing significant accumulation of the chelating agent and paramagnetic or radioactive label in the liver and spleen.

Polymers suitable for surface-modifying liposomes should be water-soluble, have a chain length longer than that of the hydrophilic polymeric moiety, and should have a molecular weight of from 500 to 40,000, and preferably from 2,000 to 20,000, daltons. Such polymers include polyethylene glycol (PEG) or polypropylene glycol (PPG) derivatives, e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or dervatives thereof, are also suitable. In addition, the protective polymer may be a block copolymer of PEG and either a polyamino acid, polysaccharide, polyamidoamine, polyethyleneamine, or polynucleotide.

The protective polymers also may be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharids or oligosaccharides (linear or branched); or carboxylated polysaccharides or oligasaccharides, e.g., reacted with derivatives of carbonic acids with resutant linking of carboxylic groups.

Such oligosaccharides may be obtained by chemical alteration of, e.g., dextran, mannan, xylan, pullulan, cellulose, chytosan, agarose, fucoidan, galactan, arabinan, fructan, fucan, chitin, pustulan, levan or pectin. In addition these polysaccharides or oligosaccharides may be heteropolymers or homopolymers of monosaccharides, e.g., glucose, galactose, mannose, galactose, deoxyglucose, ribose, deoxyribose, arabinose, fucose, xylose, xylulose, or ribulose.

The protective polymer can be bound to the lipid membrane by any one of numerous well known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive aminotion using $Na(CN)BH_3$ and a solvent mixture such as tetrahydrofuran and water in a 30:12 ration at 60° C.

The protective polymer is preferably bound to the liposome membrane via a lipid-soluble anchor as follows. The polychelating compound is mixed with lips membrane components and the protective polymer (modified to include a lipid-soluble anchor) in an organic solvent, and the mixture is desiccated to form a mixed lipid-polychelating compound-protective polymer film. This film is mixed with an aqueous liquid to form liposomes having a lipid bilayer membrane which includes a coating of labeled chelating agents on the hydrophilic polymeric moieties, and a surface layer of the protective polymer. These liposomes can then be lyophilized to form a powder that has a long stable shelf-life.

This surface layer serves two functions. First, it prevents the macrophage-monocyte system from removing these liposomes from the circulation. Second, a protective polymer such as PEG surprisingly provides an enhanced signal of the label in the case of MRI, because it improves the relaxivity of the bound Gd. The mechanism of this MRI signal enhancement is believed to be caused by an increase in the water (proton) concentration at the surface of the liposome in close proximity to the Gd atoms.

Figure 7:
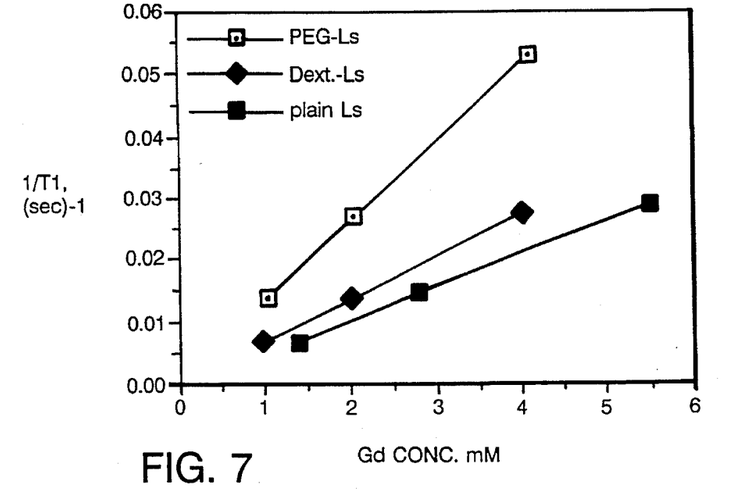
FIG. 7 is a graph showing proton relaxation of gadolinium labeled liposomes with various surface modifications.

The characteristics of such surface-modified liposomes were investigated as follows. Gd ions were introduced into liposome membranes using the amphipathic chelator DTPA-PE. As shown in FIG. 7, these plain (non-modified) liposomes (plain Ls, ■) were compared with liposomes that were surface-modified with dextran (Dext, Mw=6,000) hydrophobized using stearylamine (Dext Ls, ♦), or polyethyleneglycol (PEG, Mw=5,000) hidrophobized using phosphatidyl ethanolamine (PEG-ls, □). These amphiphilic modifiers, along with Gd-DTPA-PE and were incorporated into liposomes prepared from a mixture of egg phosphatidyl choline, cholesterol, Gd-DTPA-PE, amphiphilic modifier at a 60:25:10:5 molar ratio. Lipid suspensions were extruded through a set of polycarbonate filters with progressively smaller pore sizes until the liposomes reached a mean diameter of about 200 nm as determined by laser light scattering. Liposomes containing the polychelating compounds of the invention can be modified in the same way.

Relaxation parameters of all liposome preparations were measured using 5 MHz on a RADX NMR proton spin analyzer. In vivo imaging of the axillary/subscapular lymph node area of rabbits was performed using 1.5 Tesla on a GE Signa MRI scanner ($T_1$ weighted pulse sequence, fat suppression mode) for 2 hours after subcutaneous administration of a liposomal preparation into the paw of an anesthetized rabbit (n=3 for each group). The raw data were analyzed by image processing software (CINE program, J. Pelman, Dept. Radiology, The Massachusetts General Hospital) in order to determine relative target/nontarget (lymph node (SLN)/muscle) pixel intensity.

Figure 8:
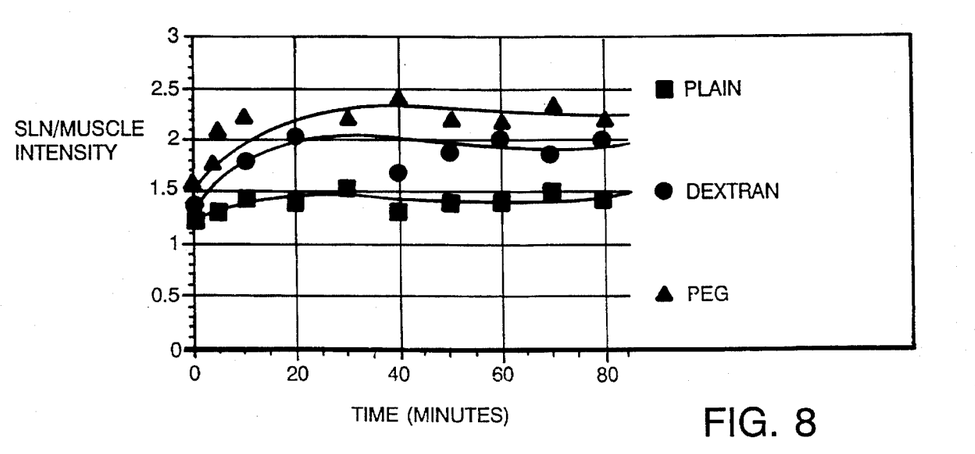
FIG. 8 is a graph showing the kinetics of MRI signal intensity from a rabbit subscapular lymph node after injection of gadolinium labeled liposomes with various surface modifications.

FIG. 7 shows that the in vitro proton molar relaxivity of the PEG-Ls is twice that of Dext-Ls and plain Ls. This fact might be explained by the presence of an increased amount of PEG-associated water protons in the close vicinity of chelated Gd ions located on the liposomal membrane. In vivo imaging after subcutaneous injection of Gd-Ls (20 mg of total lipid, 0.5 ml of saline) demonstrates that all Gd-Ls preparations are able to visualize axillar/subscapular lymph nodes within minutes. As shown in FIG. 8, the target area relative signal intensity (SLN/muscle) was found to be in the order PEG-Gd-Ls> Dext-Gd-Ls> plain Gd-Ls.

The enhanced signal of the PEG-Gd-Ls is probably due to increased relaxivity of this preparation while the Dext-Gd-Ls accumulates in lymph nodes due to possible receptor-mediated process. Dextran-enhanced accumulation of particulates and conjugates in the lymphatics has been reported previously by Takakura et al., Cancer Res., 44:2505–10 (1984). These results show that covering the liposomal surface with a protective polymer such as PEG and dextran increases the target pixel intensity 1.5 to 2 times compared to unmodified liposomes.

Use of the Polychelating Compounds

The polychelating compounds of the invention, contained in micelles or liposomes with or without targeting groups and/or other surface-modifications, can be used effectively not only as diagnostic agents, but also as therapeutic agents.

Diagnostic Agents

When labeled with paramagnetic ions or radioactive isotopes, the liposomes or micelles containing the polychelating compounds are superior contrast agents for MRI or radioscintigraphy, respectively, of the organs and tissues in the macrophage-monocyte system. If such labeled liposomes are additionally modified with a target group and/or other surface modification to achieve a longer circulation time, they can be used as contrast agents for a specific target in the body or for blood pool imaging.

A diagnostically effective amount of liposomes or micelles is administered to a patient, e.g., intravenously or subcutaneously, using standard techniques, to achieve a change in the signal of the target by at least 10 percent. The specific amount depends upon the potency of the labeling ion, weight of the patient, and clearance of the compound from the body.

A dosage of about 0.1 to 0.2 mmol Gd/kg of body weight of the patient provides a clear MR image. For radioscintraphy, injections of liposomes labeled with $^{111}$In having a radioactivity of 100 to 300 μCi in rabbits, 0.5 to 2 mCi in dogs, and 3 to 5 mCi in humans, provide a clear gamma-ray image. Other isoptopes have similar dosage ranges in humans, e.g., 5 to 15 mCi for $^{99m}$Tc, 2 to 3 mCi for $^{201}$Ti, and 2 to 10 mCi for $^{67}$Ga.

The present polychelating compound has a high potency compared to prior contrast agents, and therefore allows imaging, such as blood pool imaging, not possible with agents that require dosage volumes that are so large that they overload the vascular volume of the patient.

Therapeutic Agents

The amphipathic polychelating compounds can also be used as therapeutic agents, e.g., if labeled with a radioactive isotope such as $^{186}$Re or $^{188}$Re and used for tumor radiotherapy. Normally such isotopes cause strong, non-specific irradiation of normal tissues, which limits their clinical application. However, when linked to the polychelating compounds and incorporated into the liposomes, they can be targeted directly to desired sites to improve their clinical utility.

The accumulation of the therapeutic isotope (e.g., Re) in the tumor can proceed via two different mechanisms. First, liposomes can spontaneously accumulate in the tumor because of impaired filtration in this zone as described in, e.g., Gabizon, et al., supra. Second, Re-containing polychelating compounds can be co-immobilized on the liposome surface with tumor-specific monoclonal antibodies. The loading of antibodies in this case is much higher than when directly labeled with a low-molecular-weight chelating agent. In addition, if the target is located within the macrophage-monocyte system, e.g., in the liver, spleen, bone marrow, or lymph nodes, Re-bearing liposomes containing the polychelating compounds are automatically accumulated in these organs quickly and quantitatively.

In the case of radiotherapy, a therapeutically effective amount or dosage of liposomes or micelles is administered to a patient, e.g., intravenously or subcutaneously, using standard techniques, to achieve a certain level of radiation delivered to the target, e.g., a tumor, both in amount and distribution, without damaging surrounding healthy tissue. The specific dosage depends upon, e.g., the radioactivity of the ion, weight of the patient, and rate of targeting and clearance of the compound from the body. A dosage of about 3 to 5 times that used for imaging with radioactive isotopes, e.g., about 5 to 50 mCi, should provide effective radiotherapy.

Another therapeutic use of the polychelating compounds is for treatment of metal poisoning. For such treatments, the liposomes or micelles containing the polychelating compound are administered without any ions linked to the chelating agents, which allows the chelating agents to chelate the harmful metals in the patient's body. For example, a compound including deferoxamine as the chelating agent can be used to remove excess iron in a patient when administered intravenously in a dosage of 1 to 4 g of the deferoxamine/day. For the treatment of lead poisoning, a compound with DTPA as the chelating agent can be administered intravenously at a dosage of 0.5 to 1.0 g/day. In each case, the patient's urine metal level is monitored to determine when a sufficiently low level of the metal has been reached.

Other Embodiments

It is to be understood that while the invention has been described in conjunction with the preferred embodiments thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

What is claimed is:

1. A micelle comprising lipids and an amphipathic polychelating compound comprising a hydrophilic polymeric moiety having a backbone and a plurality of reactive side groups, a lipid-soluble anchor linked to the N terminal of said polymeric moiety, and a plurality of chelating agents linked to the side groups of said polymeric moiety, wherein said polychelating compound is linked to said lipids via said lipid-soluble anchor.

2. A liposome comprising a lipid bilayer membrane and an amphipathic polychelating compound comprising hydrophilic polymeric moiety having a backbone and a plurality of reactive side groups, a lipid-soluble anchor linked to the N terminal of said polymeric moiety, and a plurality of chelating agents linked to the side groups of said polymeric moiety, wherein said polychelating compound is bound to said membrane via said lipid-soluble anchor.

3. The liposome of claim 2, further comprising a plurality of ions, each ion being bound to one of said chelating agents.

4. The liposome of claim 2, further comprising a targeting group bound to said membrane.

5. The liposome of claim 4, wherein said targeting group is an antibody.

6. The liposome of claim 2, further comprising a protective polymer bound to said membrane.

7. The liposome of claim 6, wherein said protective polymer is water-soluble, has a chain length longer than that of said hydrophilic polymeric moiety, and has a molecular weight of from 500 to 40,000 daltons.

8. The liposome of claim 7, wherein said protective polymer is a derivative of a polyethylene glycol (PEG), polypropylene glycol (PPG), polyacrylamide, poly N-vinyl pyrrolidone, polyacrylic acid, polyalcohol, ganglioside, polyamino acid, polysaccharide, polyamidoamine, polyethyleneamine, or a copolymer or block copolymer thereof.

9. The liposome of claim 4, further comprising a protective polymer bound to said membrane.

10. A reagent kit comprising lipids and an amphipathic polychelating compound comprising a hydrophilic polymeric moiety having a main backbone and a plurality of reactive side groups, a lipid-soluble anchor linked to the N terminal of said polymeric moiety, and a plurality of chelating agents linked to the side groups of said polymeric moiety.

11. The reagent kit of claim 10, further comprising a protective polymer comprising a lipid-soluble anchor.

12. The reagent kit of claim 10, further comprising a targeting group.

13. The reagent kit of claim 10, wherein said lipids and said amphipathic polychelating compound are lyophilized.

14. A method of imaging a target region in the body of a patient, comprising administering a diagnostically effective amount of the liposomes of claim 2 to the patient, said liposomes comprising a plurality of labeling ions linked to said chelating agents on said polychelating compounds, allowing sufficient time for said liposomes to accumulate in the target region, and obtaining an image of the target region by detecting the labeling ions in the region.

15. The method of claim 14, wherein said liposomes further comprise targeting groups bound to said membranes, said groups effecting accumulation of said liposomes in the target region.

16. The method of claim 14, wherein said liposomes further comprise protective polymers bound to said membranes.

* * * * *